(12) United States Patent
Gervasi et al.

(10) Patent No.: US 9,820,859 B2
(45) Date of Patent: Nov. 21, 2017

(54) HUMERAL IMPLANT FOR A SHOULDER PROSTHESIS

(75) Inventors: Enrico Gervasi, Udine (IT); Piero Budassi, Cremona (IT); Rolf Michael Krifter, Stolzalpe (AT); Qureshi Ford, Newark (GB); Andreas Bischof, Gossau (CH); Emanuela Veronesi, Spilimbergo (IT)

(73) Assignee: LIMACORPORATE S.p.A., Udine (IT)

( * ) Notice: Subject to any disclaimer, the term of this patent is extended or adjusted under 35 U.S.C. 154(b) by 80 days.

(21) Appl. No.: 14/412,902

(22) PCT Filed: Jul. 5, 2012

(86) PCT No.: PCT/EP2012/063198
§ 371 (c)(1),
(2), (4) Date: Apr. 24, 2015

(87) PCT Pub. No.: WO2014/005644
PCT Pub. Date: Jan. 9, 2014

(65) Prior Publication Data
US 2016/0051367 A1    Feb. 25, 2016

(51) Int. Cl.
*A61F 2/40*     (2006.01)
*A61F 2/30*     (2006.01)

(52) U.S. Cl.
CPC .......... *A61F 2/4014* (2013.01); *A61F 2/4003* (2013.01); *A61F 2002/3092* (2013.01); *A61F 2002/30113* (2013.01); *A61F 2002/30224* (2013.01); *A61F 2002/30574* (2013.01); *A61F 2002/30594* (2013.01); *A61F 2002/30604* (2013.01); *A61F 2002/30879* (2013.01);
(Continued)

(58) Field of Classification Search
CPC .. A61F 2/36; A61F 2/3609; A61F 2/40; A61F 2/4014; A61F 2002/4025; A61F 2002/4081
See application file for complete search history.

(56) References Cited

U.S. PATENT DOCUMENTS 3,801,989 A * 4/1974 McKee ...................... A61F 2/32
                                                      606/86 R
3,818,514 A * 6/1974 Clark ..................... A61F 2/3609
                                                      206/438
(Continued)

FOREIGN PATENT DOCUMENTS

| EP | 1520560 A1 | 4/2005 |
| FR | 2652498 A1 | 5/1991 |
| WO | 03051238 A1 | 6/2003 |

OTHER PUBLICATIONS

Patent Cooperation Treaty International Search Report, PCT/EP2012/063198, Oct. 2012.

*Primary Examiner* — Alvin Stewart
(74) *Attorney, Agent, or Firm* — Vector IP Law Group; Robert S. Babayi

(57) ABSTRACT

The invention discloses a support element for humeral implant comprising a central body extending along an axis and at least three arms extending outwardly from the central body, the arms being transversal to said axis and bearing a ring element at their ends opposite to said central body, wherein at least a first and a second pair of arms form different angles.

13 Claims, 7 Drawing Sheets

(52) U.S. Cl.
CPC ............... *A61F 2002/4007* (2013.01); *A61F 2002/4037* (2013.01)

(56) References Cited

U.S. PATENT DOCUMENTS

| | | | | |
|---|---|---|---|---|
| 4,993,410 | A * | 2/1991 | Kimsey | A61F 2/4607 606/100 |
| 5,133,765 | A * | 7/1992 | Cuilleron | A61F 2/0095 206/363 |
| 5,147,366 | A * | 9/1992 | Arroyo | A61B 17/8808 606/92 |
| 5,405,394 | A * | 4/1995 | Davidson | A61L 27/306 623/18.11 |
| 5,507,819 | A * | 4/1996 | Wolf | A61F 2/4081 623/19.11 |
| 5,674,225 | A * | 10/1997 | Muller | A61B 17/1659 606/100 |
| 5,735,905 | A * | 4/1998 | Parr | A61F 2/3609 623/23.11 |
| 5,865,850 | A * | 2/1999 | Matthews | A61F 2/3609 623/22.43 |
| 5,885,295 | A * | 3/1999 | McDaniel | A61B 17/8802 606/85 |
| 6,110,179 | A * | 8/2000 | Flivik | A61B 17/8808 606/94 |
| 6,344,060 | B1 * | 2/2002 | Schmotzer | A61F 2/30724 606/95 |
| 6,585,771 | B1 * | 7/2003 | Buttermilch | A61B 90/94 623/21.11 |
| 6,669,734 | B2 * | 12/2003 | Spotorno | A61F 2/30724 623/23.15 |
| 6,797,007 | B1 * | 9/2004 | Von Chamier | A61F 2/34 623/22.45 |
| 7,445,638 | B2 * | 11/2008 | Beguin | A61F 2/4014 623/19.12 |
| 7,879,042 | B2 * | 2/2011 | Long | A61F 2/4607 606/99 |
| 8,361,162 | B2 * | 1/2013 | Berry | A61F 2/30724 623/22.12 |
| 8,876,908 | B2 * | 11/2014 | Katrana | A61F 2/4003 623/19.11 |
| D745,678 | S * | 12/2015 | Courtney | D24/155 |
| 9,248,021 | B1 * | 2/2016 | Termanini | A61F 2/30721 |
| 9,326,865 | B2 * | 5/2016 | Katrana | A61F 2/4014 |
| 9,364,334 | B2 * | 6/2016 | Katrana | A61F 2/4014 |
| 2004/0015238 | A1 * | 1/2004 | Buehler | A61B 17/8808 623/22.12 |
| 2004/0220673 | A1 * | 11/2004 | Pria | A61F 2/4081 623/19.12 |
| 2004/0220674 | A1 * | 11/2004 | Pria | A61F 2/40 623/19.12 |
| 2006/0167557 | A1 * | 7/2006 | Terrill | A61F 2/3609 623/22.43 |
| 2006/0200249 | A1 * | 9/2006 | Beguin | A61F 2/4014 623/19.14 |
| 2008/0183297 | A1 * | 7/2008 | Boileau | A61F 2/4081 623/19.14 |
| 2009/0299484 | A1 * | 12/2009 | Dietrich | A61F 2/0095 623/22.4 |
| 2010/0114326 | A1 * | 5/2010 | Winslow | A61F 2/3601 623/23.42 |
| 2010/0179664 | A1 * | 7/2010 | Brooks | A61F 2/4637 623/22.41 |
| 2010/0274359 | A1 * | 10/2010 | Brunnarius | A61F 2/30734 623/19.13 |
| 2011/0144756 | A1 * | 6/2011 | Bickley | A61F 2/40 623/18.11 |
| 2012/0253467 | A1 * | 10/2012 | Frankle | A61F 2/40 623/19.11 |
| 2013/0018476 | A1 * | 1/2013 | Katrana | A61F 2/4003 623/19.14 |
| 2013/0184834 | A1 * | 7/2013 | Brooks | A61F 2/30 623/23.42 |
| 2013/0261629 | A1 * | 10/2013 | Anthony | A61F 2/4014 606/80 |
| 2014/0094927 | A1 * | 4/2014 | Weeden | A61F 2/32 623/22.21 |
| 2014/0358239 | A1 * | 12/2014 | Katrana | A61F 2/4003 623/19.14 |
| 2014/0358240 | A1 * | 12/2014 | Katrana | A61F 2/4003 623/19.14 |
| 2015/0216667 | A1 * | 8/2015 | Monaghan | A61F 2/30 623/23.42 |
| 2015/0272740 | A1 * | 10/2015 | Wakiyama | A61F 2/3609 623/23.11 |
| 2016/0074167 | A1 * | 3/2016 | Vautrin | A61F 2/30942 623/23.52 |

\* cited by examiner

HUMERAL IMPLANT FOR A SHOULDER PROSTHESIS

TECHNICAL FIELD

The present invention relates to orthopedic implants, in particular shoulder prostheses.

BACKGROUND ART

A natural shoulder joint may undergo degenerative changes caused by a variety of reasons. When these degenerative changes become so far advanced and irreversible, it may ultimately become necessary to replace a natural shoulder joint with a prosthetic shoulder joint. In the traditional implantation of a shoulder joint prosthesis, the natural head portion of the humerus is resected and a cavity is created in the intramedullary canal of the host humerus for accepting a humeral component. The humeral component generally includes a stem, and a head portion, which is used to replace the natural head of the humerus. Once the humeral component has been implanted, the glenoid cavity positioned at the scapula may also be resected and shaped to accept a glenoid component. The glenoid component generally includes an articulating surface or cup which is engaged by the head portion of the humeral component. Modular designs for the humeral and glenoid components are currently available for the traditional shoulder arthroplasty, and components of different sizes or shapes are at the disposal of the surgeon performing the operation.

The traditional shoulder joint implantation requires that the rotator cuff muscles be present and functioning normally. When this is not the case, a reverse shoulder prosthesis may be preferable. In the reverse shoulder prosthesis, the humeral component includes a stem, and a cup connected to the stem. The glenoid component supports a head which articulates with the cup.

It is not always practical to determine well in advance of the procedure whether a reverse or traditional shoulder prosthesis should be used. It is, therefore, desirable to provide a selection of modular components that can be combined for use in traditional as well as reverse shoulder arthroplasty, with the goals of increasing flexibility and choice and for providing interchangeable and easy to use components that are also cost effective.

When the glenoid cavity is intact, which is the case in the event of a comminuted fracture, shoulder prosthesis includes a humeral element fixed into the medullary cavity of the humerus provided with a male implant having spherical shape able to cooperate directly with the glenoid cavity.

In the case of destruction of the glenoid cavity, the prosthesis consists in an support implanted in the glenoid and provided with an insert male or female intended to cooperate with a corresponding shape arranged at the humeral element. Different kinds of prosthesis are known in the art.

FR2652498 discloses a modular humeral implant comprising an anchoring stem, provided at its upper end with a head having a recess arranged to receive a male or a female insert.

One disadvantage of this anchoring stem is that it requires, on the basis of the dimensions of the head of said stem, a significant resection of cancellous bone.

In addition, the positioning of the stem leads to modify the original positioning of the humeral head and of its center of rotation, which could lead to a fracture of the humerus metaphyseal area.

In general, the problems related to humeral component with a stems are the following: the offset between the centre of rotation of the head and the axis of the diaphysis, implantation surgery is more difficult and the required time is longer compared to stemless procedures, postoperative complications are dominated by fractures, the removal of the stem in case of revision surgery is necessary.

Different solutions have been proposed to avoid these complications: the use of modular prosthesis and the humeral head resurfacing. In an effort to reduce stem complications and to avoid the loosening of the humeral component, stemless prosthesis with methaphysial fixation are being developed such as that illustrated in EP1520560. The goal of the stemless prosthesis is to restore the anatomy of the humeral head without need of a stem, with automatic centering, through a simple and reproducible technique, with the preservation of the bone stock and an adequate exposure of the glenoid. The indications for a stemless prosthesis humeral implant are the same as the indications for traditional hemiarthroplasty, total shoulder replacement, or even humeral head resurfacing. The stemless prosthesis could be implanted in cases of significant bone loss, for example in advanced avascular necrosis. The main indication for stemless implantation remains painful gleno-humeral ostheoartris.

The indications for placement of a glenoid component are identical as in traditional total shoulder arthoplasty. The controindications on the stemless use are osteopenia, acute proximal humeral fractures and active infections.

EP1520560 discloses an anatomic humeral prosthesis consisting of a removable support for metaphyseal fixation and a humeral head, a male or a female insert able to cooperate with glenoid cavity, fixed to the removable support through a intermediate neck, i.e. a Morse taper. It further comprises an anchoring stem. The removable support has the shape of a basket provided with a circular seat with a through-opening and comprising at least 3 identical branches substantially in the shape of an arc or a circle, which are spaced apart at intervals and give said support a general hemispherical shape.

The prosthesis described in EP1520560 need to be removed from the patient in case of conversion from anatomical configuration to reverse.

DISCLOSURE OF INVENTION

The aim of the present invention is to provide a novel humeral implant overcoming the above mentioned drawbacks. In particular, it is an object of the present invention to provide an humeral implant that achieves an anatomical optimal distribution of loads and that do not need removal from the patient in case of conversion from the anatomical configuration to the reverse.

According to the present invention, these aims is achieved by a humeral implant according to claim 1.

The invention relates more specifically to a humeral implant shaped to receive either a male insert or a female insert, depending on the situation encountered at the shoulder joint to be treated.

In the following description, the term "male insert" means an adaptor necessary to connect a prosthetic humeral head, in practice a sphere or hemisphere, intended to cooperate with the glenoid cavity, either directly or by way of a support provided with a corresponding female form, in practice a cup.

Similarly, the term "female insert" means a female part, in practice a reverse liner intended to cooperate with a male part, in practice a sphere or hemisphere, and arranged on a support which is itself implanted in the glenoid region.

BRIEF DESCRIPTION OF THE DRAWINGS

A preferred embodiment is hereinafter disclosed for a better understanding of the present invention, by mere way of non-limitative example and with reference to the accompanying drawings, in which.

BEST MODE FOR CARRYING OUT THE INVENTION

Figure 1:
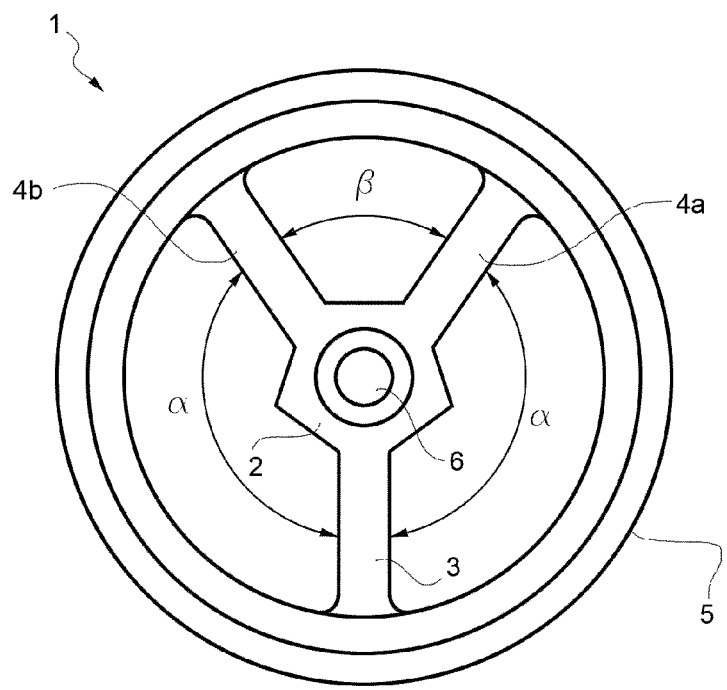
FIG. 1 is a planar view of the support element according to the present invention.
Figure 2:
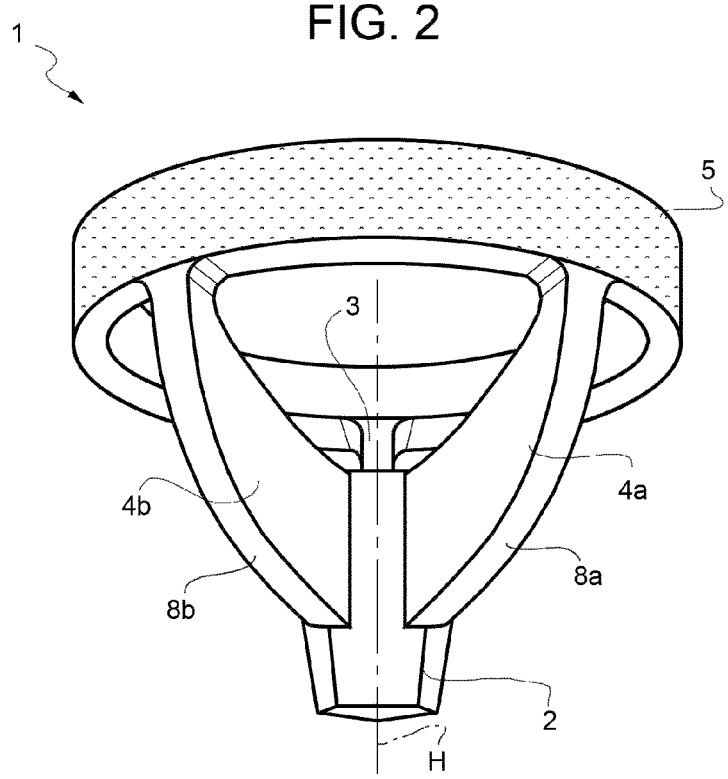
FIGS. 2 and 3 are perspective views that show the support element according to the present invention.
Figure 3:
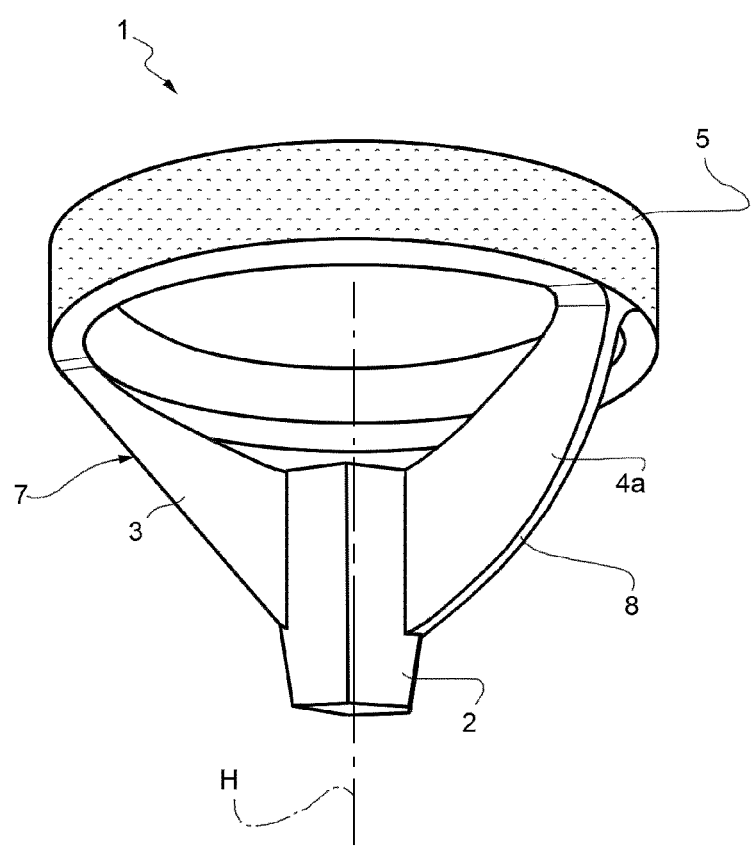

FIGS. 1-3 indicate with numeral 1 as a whole a support element for an humeral implant according to the invention.

The support element 1 comprises a central body 2 extending along an axis H. The central body 2 has three arms 3, 4a and 4b extending outwardly from the central body 2 and transversely positioned with respect to the axis H. The number of the arms may vary from 3 to 5.

The three arms 3, 4a and 4b bear a ring element 5 at their ends opposite to said central body 2. The ring element 5—according to a first embodiment of the invention—comprises a cylindrical tubular body coaxial to axis H. The tubular body is one piece with arms 3, 4a and 4b.

According to a different embodiment (FIG. 4), tubular body comprises a first cylindrical portion 5a coaxial to axis H and a second integral cylindrical portion 5b coaxial to a different axis H1 forming an angle γ with axis H. Arms 3, 4a and 4b and are spaced one with respect to the other along the axis H so that at least a first pair of arms 3-4a or 3-4b and a second pair of arms 4a-4b form different angles α and β with respect the axis H (see FIG. 1). In particular, the angle β is formed between arms 4a and 4b and the angles α are formed between the arms 3 and 4a or 4b. These angles may vary in the range between 50° and 180° for β and between 90° and 155° for α, preferably between 60° and 80° for β and between 140° and 150° for α.

The arm 3 has an outer rim 7 on the side opposite to ring element 5 that is rectilinear and arms 4a, 4b have an outer rim 8a, 8b on the side opposite to ring element 5 that is curvilinear.

All the arms 3, 4a and 4b have a transversal section tapering from the central element 2 towards the ring element 5. In particular, the arms 3, 4a, 4b have, at the portion proximal to the ring element 5, a transversal section that is 20-40% smaller than their transversal section at the portion distal from the ring element 5.

The central body 2 is further provided with an concentric, coaxial with axis H, threaded blind hole 6 that opens on the side facing ring element 5. The blind hole 6 can be used to accommodate a tool (not shown) used for the insertion and removal of the support element 1.

The support element is made of titanium alloy so as to achieve the maximum bio compatibility.

Figure 7:
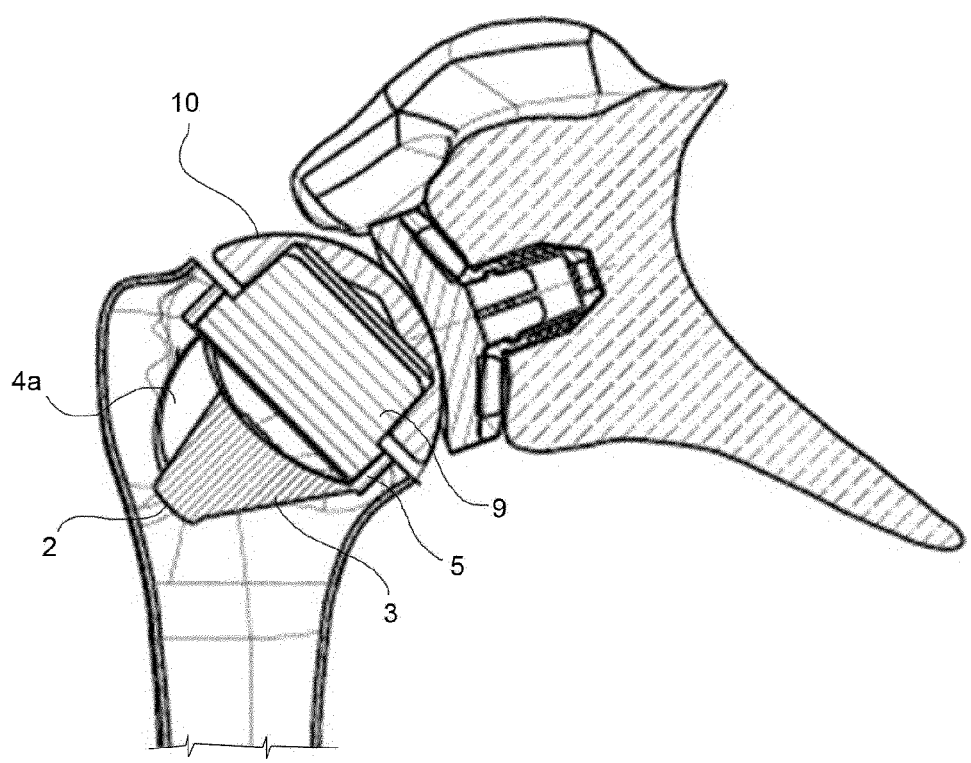
FIG. 7 is a planar view of the humeral implant of FIG. 5 implanted into the humerus.
Figure 8:
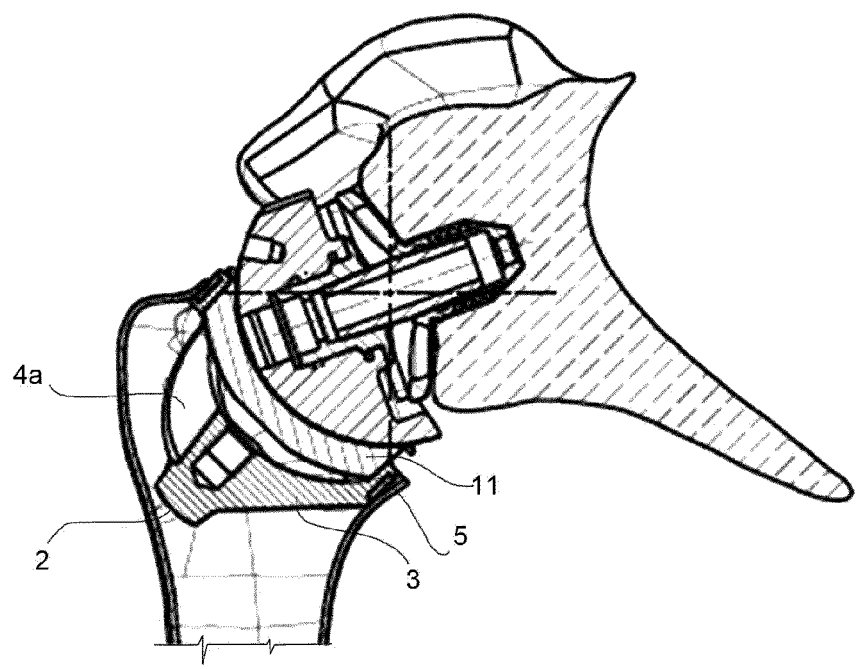
FIG. 8 is a planar view of the humeral implant of FIG. 6 implanted into the humerus.

The humeral implant according to the present invention is implanted by resecting one end of the bone, creating cavities to accommodate the arms 3, 4a and 4b and the ring element 5 and placing the support element 1 in the above respective cavities (FIGS. 7 and 8).

The support element is placed with respect to the bone so that to place the arm 3 provided with linear rim 7 in the portion of the humerus head facing the glenoid surface. In this way, an anatomical distribution of the load is achieved.

Accordingly, the ring element 5 allows the peripheral fixation of the implant on the resected humeral head and the arms 3, 4a and 4b allow the fixation to the cortex and the load transmission from the prosthesis to the bone following the natural pattern.

The presence of the ring element 5 and the specific positioning of the arms 3, 4a and 4b allow an improved transmission of loads from the prosthesis to the bone as well as the stability of the implant and the prevention of the rotation.

In the prosthesis of the prior art, the load is transmitted to the spongy bone of the humerus through a central component; the contact between the prosthesis head and the resected surface allows a small load transmission to the peripheral cortex of the bone.

The literature (R. H. Cofield, J. W. Sperling, Revision and complex shoulder arthroplasty, Lippincott Williams and Wilkins Ed) reports that there must be a macrointerlock between the prosthesis and the bone. This means that there must be sufficient bone in all areas to bear stresses: this often requires impaction grafting of the cancellus bone. The distribution of the forces should be such that stress-guided remodelling does not alter the bone significantly with time.

This means also that the best fixation of the prosthesis is the one that allow a transmission of load to the bone that reproduce the natural one.

The load transmission to the bone is related to the distribution of the bone trabeculae. In the humerus is possible to identify five different areas of trabeculae distribution (M. C. Hall, M. Rosser, The structure of the upper end of the humerus with reference to osteoporotic changes in senescence leading to fractures, Canad. Med. Ass. J., Feb. 9, 1663, vol. 88; study performed on osteoporotic humeri).

In case of a prosthesis implantation it is very important to allow the load transmission from the prosthesis to the bone. Indeed if the bone is loaded it remains alive and it is possible to have osteointegration. Otherwise, if the bone is not under load it is possible to have a bone resorption and finally a prosthesis mobilization.

The ring element 5 is able to receive both a male insert 9 or female insert 10. This has in particular the advantage that removal of the humeral implant is not necessary to convert the prosthesis from the anatomical application to the reverse.

Figure 4:
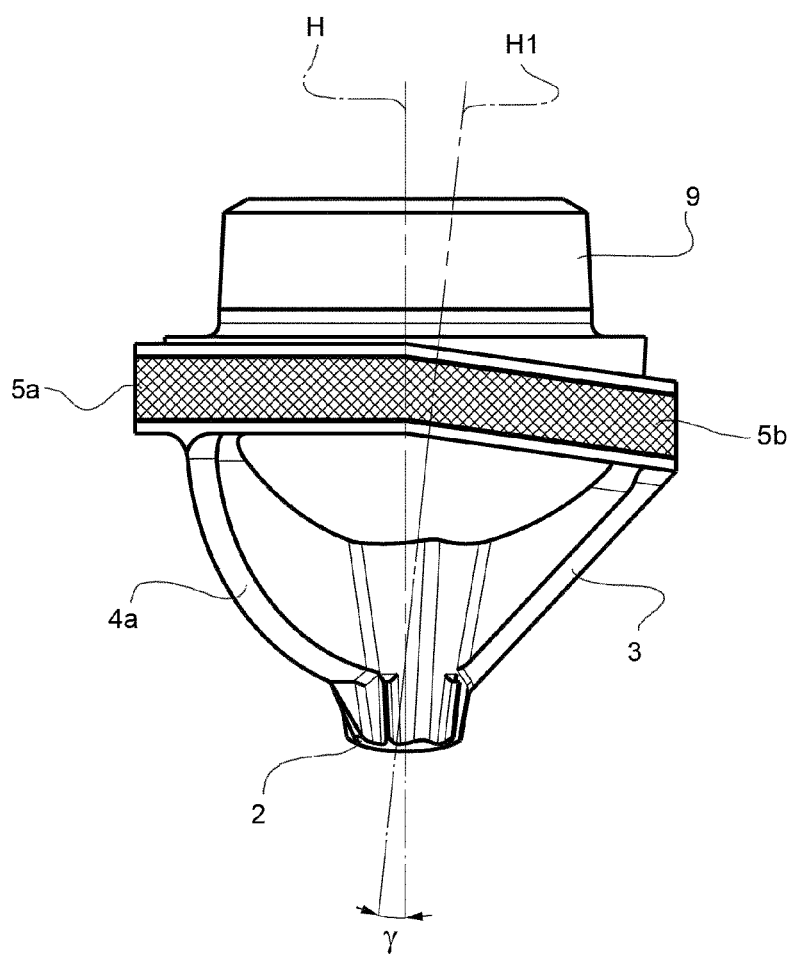
FIG. 4 is a perspective views that show the support element according to the present invention in its anatomical configuration mounting a male insert.
Figure 5:
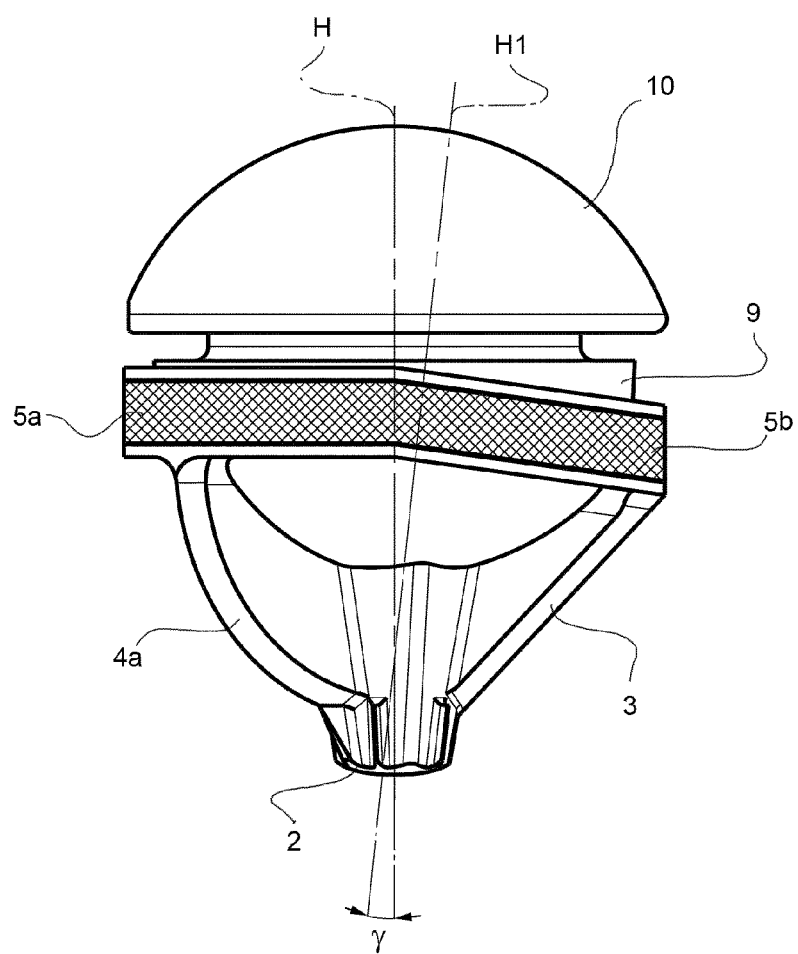
FIG. 5 is a perspective views that show the support element according to the present invention in its anatomical configuration mounting a male insert and a humeral head.

In case of the anatomical configuration, as shown in FIGS. 4 and 5, a male insert is mounted on the ring 5. The male insert will then be connected with the humeral head 10.

Figure 6:
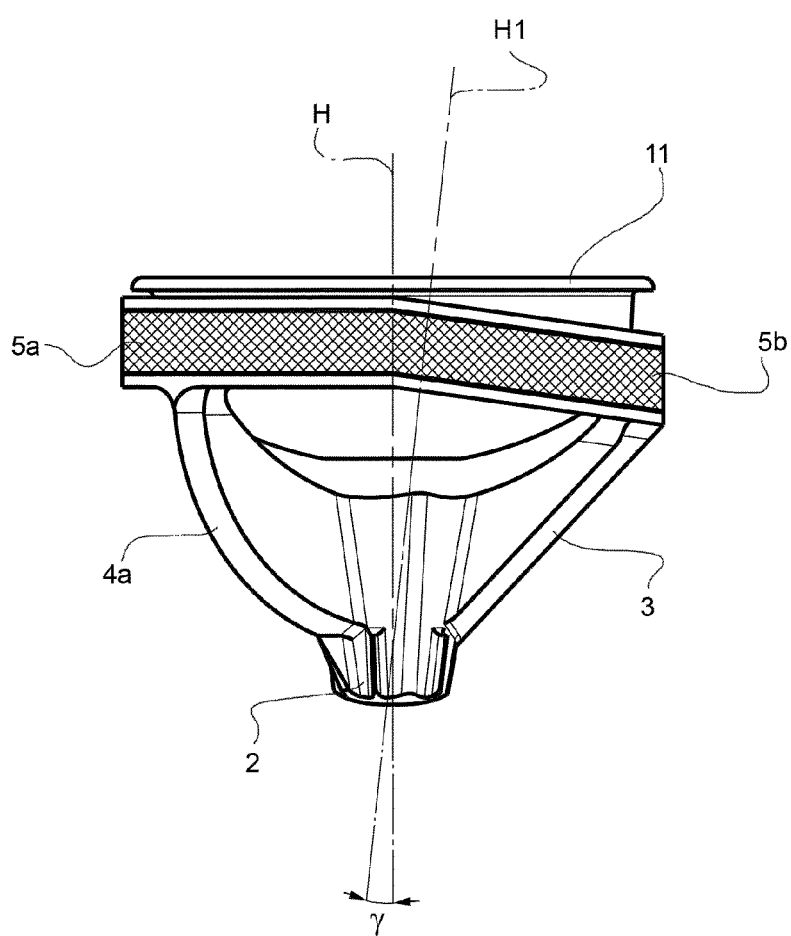
FIG. 6 is a perspective views that show the support element according to the present invention in its reverse configuration mounting a female insert.

In case of the inverse configuration, a female insert 11 is mounted on the ring 5, as shown in FIG. 6.

Moreover, the ring element 5 has a trabecular structure in order to increase the primary stability of the support element 1 as well as its osteointegration. In this way the support element 1 may be used also in case of implantation reverse prosthesis, in which the loads to be borne are higher than in case of anatomic prosthesis.

Moreover, in case of conversion from anatomic prosthesis to reverse one, for example because of a cuff tear, it will be possible to leave the osteointegrated support element 1 in its position and simply remove the male insert 9 and connecting female insert 10.

The invention claimed is:

1. Support element for humeral implant comprising a central body extending along an axis and at least three arms extending outwardly from said central body, said arms being transversal to said axis and bearing a ring element at their ends opposite to said central body wherein an angle $\alpha$ formed between a first and a second adjacent arms being different from an angle $\beta$ formed between a third arm that is adjacent to the first arm and the second arm, wherein there are no other arms between adjacent arms.

2. Support element according to claim 1, wherein said angle $\alpha$ varies between 90° and 155°.

3. Support element according to claim 2, wherein said angle $\alpha$ varies between 140° and 150°.

4. Support element according to claim 1, wherein said angle $\beta$ varies between 50° and 180°.

5. Support element according to claim 4, wherein said angle $\beta$ varies between 60° and 80°.

6. Support element according to claim 1, wherein at least one of said arms has an outer rim on the side opposite to ring element—that is rectilinear.

7. Support element according to claim 1, wherein at least two of said arms have an outer rim on the side opposite to ring element that is curvilinear.

8. Support element according to claim 1, wherein said arms have a transversal section tapering from the central body towards the ring element.

9. Support element according to claim 8, wherein the transversal section of said arms at the portion proximal to the ring element is 20-40% smaller than the transversal section at the portion distal from the ring element.

10. Support element according to claim 1, wherein said central body is provided with an internal coaxial threaded blind hole.

11. Support element according to claim 1 wherein said ring element has a trabecular structure.

12. Support element according to claim 1 made of trabecular titanium.

13. Support element for humeral implant comprising a central body extending along an axis and at least three arms extending outwardly from said central body, said arms being transversal to said axis and bearing a ring element at their ends opposite to said central body wherein at least a first and a second pair of arms form different angles, wherein said ring element comprises a first cylindrical portion coaxial to said axis and a second integral cylindrical portion coaxial to a further axis forming an angle $\gamma$ with said axis.

* * * * *